(12) United States Patent
Dudding et al.

(10) Patent No.: US 7,720,543 B2
(45) Date of Patent: May 18, 2010

(54) SYSTEM AND METHOD FOR TELEMETRY WITH AN IMPLANTABLE MEDICAL DEVICE

(75) Inventors: Charles H. Dudding, Lino Lakes, MN (US); Javaid Masoud, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 805 days.

(21) Appl. No.: 11/334,914

(22) Filed: Jan. 19, 2006

(65) Prior Publication Data

US 2007/0167996 A1  Jul. 19, 2007

(51) Int. Cl.
*A61N 1/08* (2006.01)

(52) U.S. Cl. .............................. 607/60; 607/16; 607/32

(58) Field of Classification Search ............ 340/539.28, 340/870.16; 370/345; 600/302; 607/9, 27, 607/60, 32; 709/230; 67/32
See application file for complete search history.

(56) References Cited

U.S. PATENT DOCUMENTS

| | | | | |
|---|---|---|---|---|
| 6,046,674 A | * | 4/2000 | Irwin et al. ............. | 340/539.28 |
| 6,141,588 A | * | 10/2000 | Cox et al. ....................... | 607/9 |
| 6,443,891 B1 | * | 9/2002 | Grevious ..................... | 600/302 |
| 6,668,196 B1 | | 12/2003 | Villegas et al. | |
| 6,758,810 B2 | * | 7/2004 | Lebel et al. ................. | 600/300 |
| 6,897,788 B2 | * | 5/2005 | Khair et al. ............. | 340/870.16 |
| 6,993,393 B2 | * | 1/2006 | Von Arx et al. ............... | 607/60 |
| 7,280,872 B1 | * | 10/2007 | Mosesov et al. ............... | 607/60 |
| 2002/0013614 A1 | * | 1/2002 | Thompson ................... | 607/60 |
| 2002/0026224 A1 | | 2/2002 | Thompson et al. | |
| 2003/0009203 A1 | * | 1/2003 | Lebel et al. .................... | 607/60 |
| 2003/0074035 A1 | * | 4/2003 | Bornhoft et al. .............. | 607/60 |
| 2004/0158299 A1 | | 8/2004 | Patrias | |
| 2004/0215272 A1 | * | 10/2004 | Haubrich et al. .............. | 607/27 |
| 2005/0107841 A1 | | 5/2005 | Meadows et al. | |
| 2006/0062196 A1 | * | 3/2006 | Cai et al. ..................... | 370/345 |
| 2007/0060977 A1 | * | 3/2007 | Spital .......................... | 607/60 |
| 2007/0271387 A1 | * | 11/2007 | Lydon et al. ................. | 709/230 |
| 2008/0293422 A1 | * | 11/2008 | Kang et al. ................. | 455/446 |

FOREIGN PATENT DOCUMENTS

EP  1495783 A1  7/2003

OTHER PUBLICATIONS

Axelson, Jan. Serial Port Complete: Programming and Circuits for Rs-232 and Rs-485 Links and Networks. 1998.*
Kravets et al. "Application-driven Power Management for Mobile Communication." Wireless Networks. 2000. p. 263-277.*

\* cited by examiner

*Primary Examiner*—Carl H Layno
*Assistant Examiner*—Luther G Behringer
(74) *Attorney, Agent, or Firm*—Michael J. Ostrom; Stephen W. Bauer

(57) ABSTRACT

An implantable medical device (IMD) includes a telemetry module to communicate with an external device according to a given protocol. To establish a communication session, the IMD will extend active periods of reception on a given channel when some confirmed data is received from the external device. In addition, once a session has been opened, the programmer transmits a short data set (or preamble) for each cycle which the IMD is set to receive. This data set indicates whether additional data will or will not be sent. If no additional data is to be sent during that cycle, then the IMD powers down the receiver for that cycle.

19 Claims, 12 Drawing Sheets

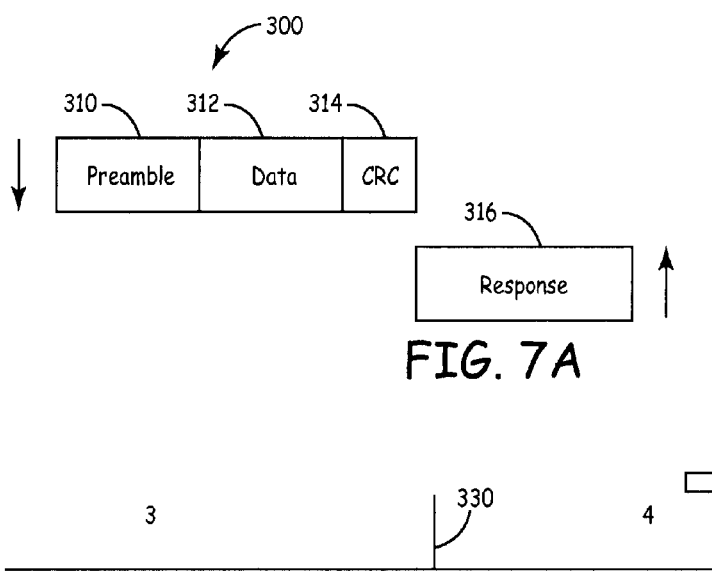
FIG. 7A
FIG. 7B
FIG. 7C

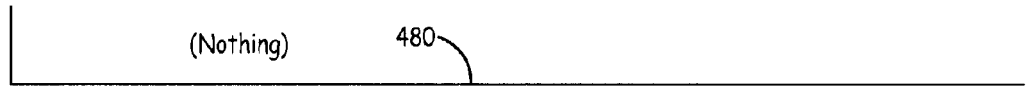
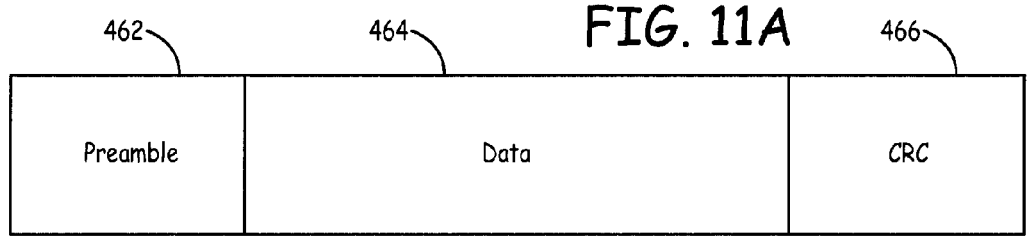
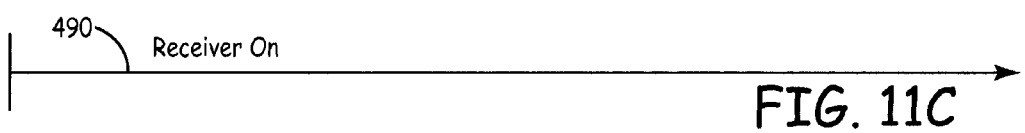
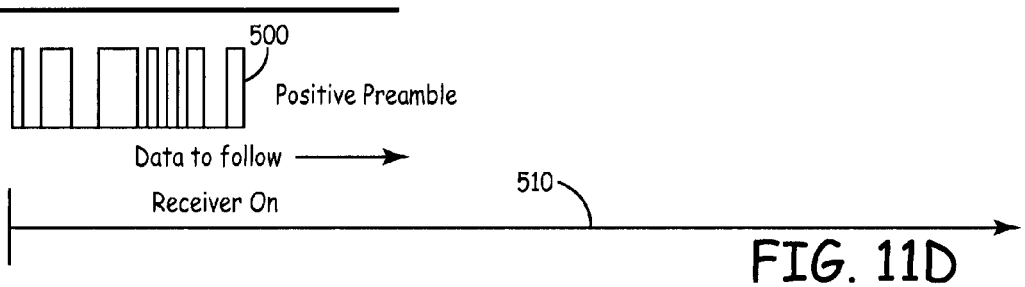
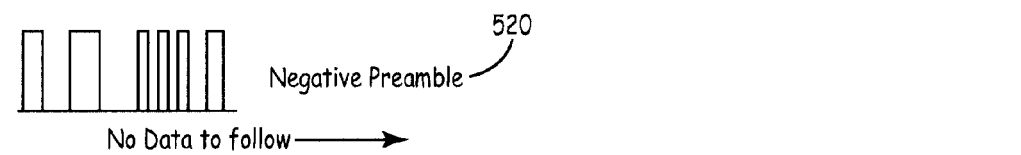
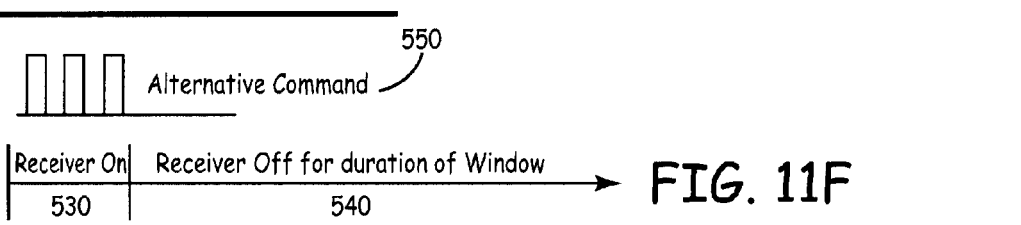

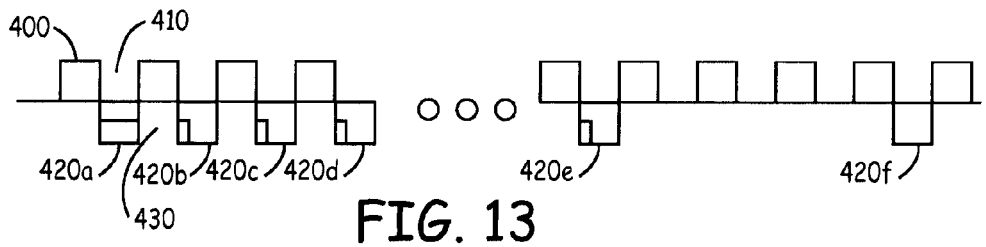
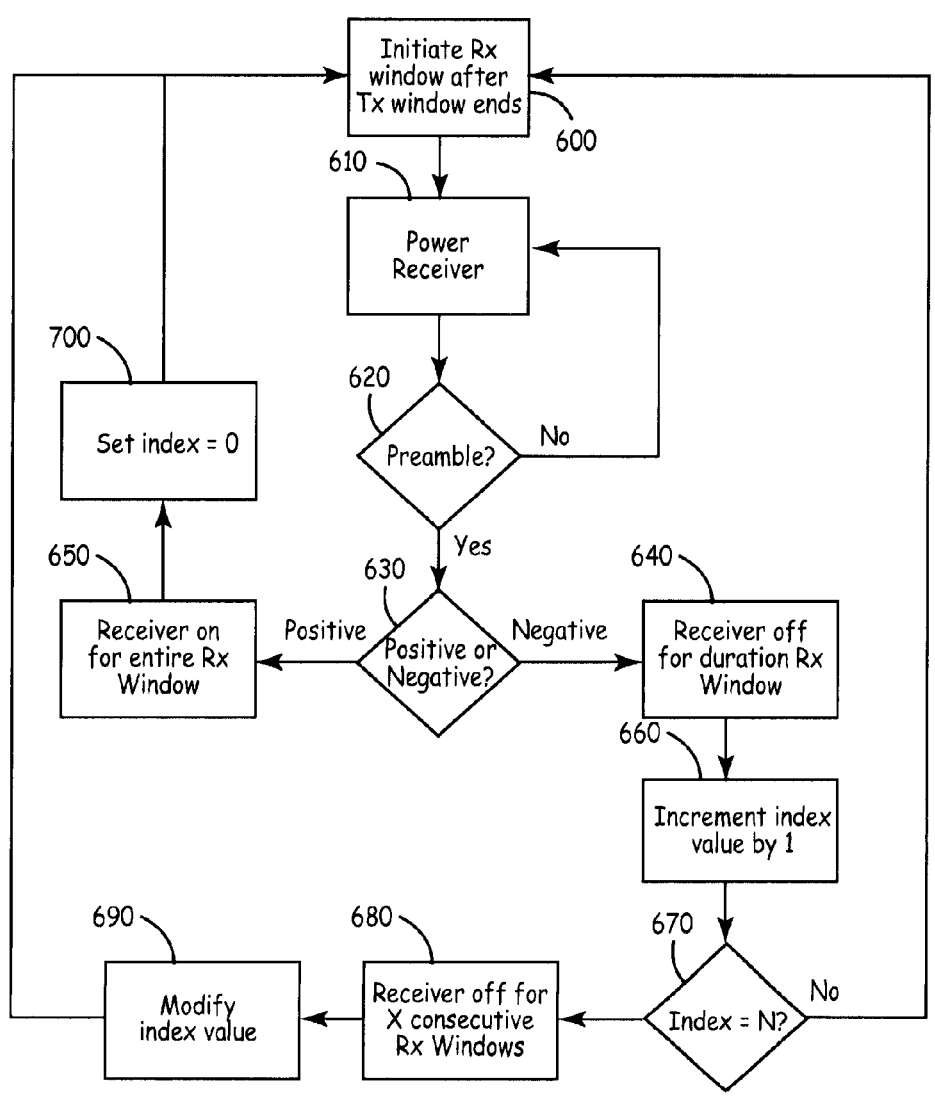

SYSTEM AND METHOD FOR TELEMETRY WITH AN IMPLANTABLE MEDICAL DEVICE

BACKGROUND

1. Field of the Invention

The present invention relates generally to medical devices and, more specifically, to implantable medical devices that include telemetry capabilities.

2. Description of the Related Art

There are a wide variety of implantable medical devices (IMDS) that sense data and/or provide therapies. In the cardiac arena, there are implantable loop recorders (ILRs) that are implanted subcutaneously to record cardiac data. So called "low power" devices provide pacing therapies and are often referred to as implantable pulse generators (IPGs) or pacemakers. "High power" devices provide cardioversion and/or defibrillation therapy and are referred to as implantable cardioverter/defibrillators (ICDs). ICDs will often also having pacing capabilities and, as used herein, may take either form. Many other types of cardiac devices are available and, of course, implantable devices are useful in many other contexts such as neurology, diabetes, and pain management, to name a few. While particular reference is made to ICDs for illustrative purposes, it should be appreciated that the present invention is not so limited and applies to a wide variety of implantable medical devices.

A typical ICD or IPG is implanted having a non-rechargeable battery with an expected lifetime of 3-15 years, with 5-10 years being most common. This has been made possible with advancements in battery and capacitor technology, as well as reducing power requirements of the components within the device. At the same time, many more features, therapies and capabilities are provided in modern IMDs that simply require additional power. Therefore, with these considerations in mind, power management is an important aspect in the design and manufacture of IMDs.

IMDs have had telemetry capabilities for quite some time. In the past, a programming head having an inductive coil was placed in contact with the patient's skin proximate the site of implant. Data was transferred between the programming head and the IMD through inductive coupling over this very short distance. The programming head was connected to a device such as a medical device programmer that was able to receive and display data from the IMD as well as program various functions of the IMD.

Recently, there has been a trend to move to so-called "distance telemetry," wherein the IMD communicates with an external device via radio frequency communication. This permits communication with the IMD without requiring the presence of a programming head during the communication session. In-office follow-ups are easier and less cumbersome, but this also permits a patient's IMD to communicate in virtually any environment without encumbering the patient. For example, a patient may be provided with a home monitor that communicates with the IMD via RF communication, and transmits this data to a central server (e.g., the Medtronic CareLink™ database). Similarly, the IMD may communicate with any number of external devices in this manner.

While providing many benefits, distance telemetry also utilizes scarce power resources. This is a consideration both in transmitting data as well as when "listening for" and actually receiving data.

BRIEF DESCRIPTION OF THE DRAWINGS

FIGS. 6-8 are schematic diagrams illustrating a communication exchange to open a session.

FIG. 11 is a schematic diagram illustrating various data transmitted from a programmer.

FIG. 13 is a schematic diagram representing powering down a receiver during certain time periods.

FIG. 14 is a flowchart describing a process of determining when to enter prolonged periods of time wherein the receiver is powered down during synchronous communication sessions.

DETAILED DESCRIPTION

Figure 1:
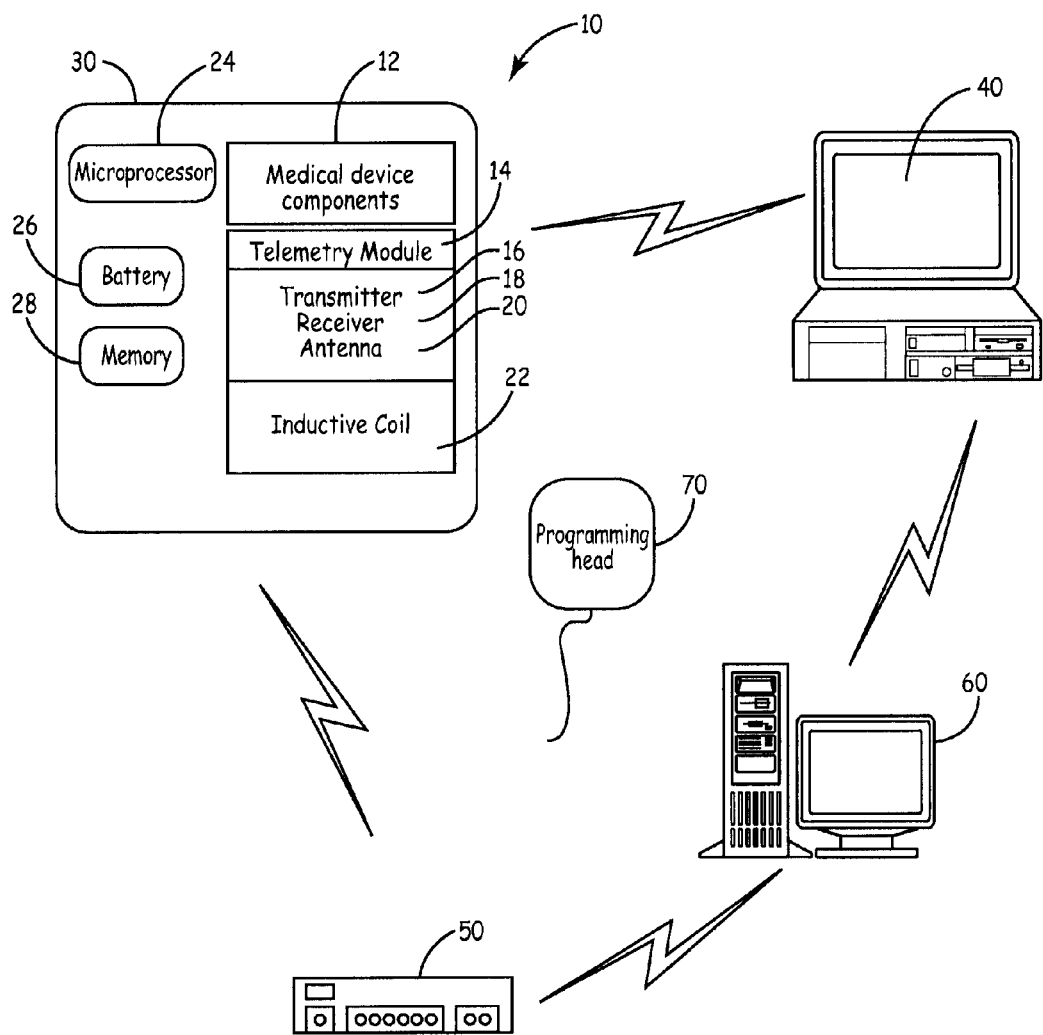
FIG. 1 is a schematic diagram illustrating an implantable medical device (IMD) and various external devices.

FIG. 1 is a schematic illustration of an implantable medical device (IMD) 10. The IMD 10 includes a hermetically sealed housing 30 containing various operative components and is intended to be implanted subcutaneously or submuscularly. The various device components 12 provided to operate the IMD 10 will vary depending upon the type of device and may include, for example, a pulse generator, capacitors, leads, sensors, accelerometers and various other components. A microprocessor 24, battery 26 and memory 28 are typically provided.

The IMD 10 includes a telemetry module 14 which further includes a transmitter 16, receiver 18, and antenna 20. It will be appreciated that a transceiver may be a discrete component that performs the functions of both the receiver and transmitter, and that the use of the latter terms will include the former. In some embodiments, the IMD 10 includes an inductive coil 22. The IMD 10 may communicate with a variety of external devices including, but not limited to, a programmer 40 or external medical device (EMD) 50, such as a home monitor. The EMD 50 may provide data to a central server 60, which then provides access to the data to caregivers in a variety of formats including access through the programmer 40. The EMD 50 may communicate directly with the programmer 40 or other display terminal. A programming head 70 may be coupled with the programmer 40 and/or the EMD 50 to facilitate telemetry in certain embodiments.

In general, the telemetry module 14 of the present invention communicates via RF signals to provide distance telemetry over a range of 3-20 meters, with significantly greater distances possible in some embodiments. The telemetry module 14 does not preclude, and typically will include, the capability of other telemetry formats, such as inductive coupling.

Figure 2:
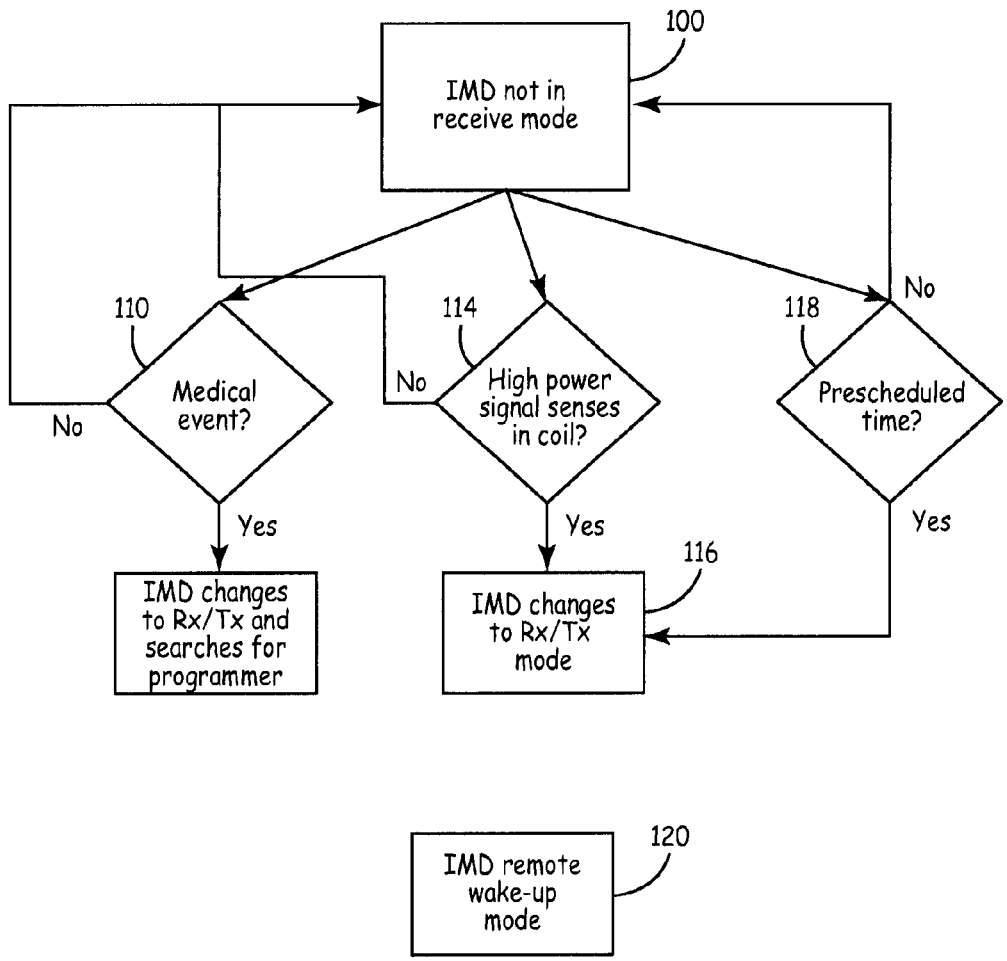
FIG. 2 is a flowchart describing a change in state of the IMD from a non-receiving mode to a receiving mode.

FIG. 2 is a flowchart describing a process for determining a communication mode for the IMD 10. As indicated, the finite power supply of the battery means that power management is an issue. As such, the easiest communication mode may be impractical due to power considerations. That is, simply maintaining the receiver 18 in an "on" or "listening" mode at all times would generally consume too much power and, as telemetry occurs infrequently, this power would effectively be wasted.

As such, the IMD 10 will have the receiver 18 powered down 100 and therefore not be in a "receive" mode during a vast majority of the operating lifetime of the device 10. In order to effectively provide telemetry, the IMD 10 must enable the receiver 14 at appropriate times. One such time is when a medical event 110 occurs that causes the IMD 10 to initiate telemetry. When such an event occurs, the IMD 10 will transmit a communication to identify any nearby programmer 40 or EMD 50 capable of receiving a transmission. A variety of message formats or protocols may be utilized (including simply transmitting data without confirmation that it is received). In general, the IMD 10 identifies its presence, the need to communicate, and requests a response from the programmer 40 or EMD 50. As such, after transmitting the message, the receiver is powered on for a period of time. This process may be repeated numerous times.

While operating the RF receiver when unnecessary tends to consume more power than desired, frequently monitoring the status of the inductive coil 22 requires comparatively little power. As such, the IMD 10 will sense the status of the inductive coil 22 at regular intervals (e.g., 250 ms). If a high power signal is sensed in the coil 22, this indicates that a programming head 70 (or similar inductive device) has been placed proximate the IMD 10 to initiate telemetry 114.

In some devices, this will initiate a short-range telemetry session wherein data is communicated via inductive coupling. In this manner, the programmer 40 may be used to communicate with the IMD 10 and send/receive data via inductive coupling or, once so linked, instruct the IMD 10 to utilized distance (e.g., RF) telemetry.

In another embodiment, the high power signal sensed in the coil 22 triggers 116 the IMD to activate distance telemetry. In other words, the inductive coupling is not necessarily used to send/receive data but just to initiate a distance telemetry session. The IMD 10 will also activate the receiver 18 for pre-scheduled telemetry sessions. When a predetermined time occurs, the IMD 10 begins listening for, or transmitting to, a device that is expected to be within range. Finally, in some embodiments there are protocols provided for remote RF "wake-up" 120 of an IMD 10. That is, an RF signal is transmitted to the IMD 10 that causes the device to fully power the receiver 18 and/or transmitter 16. Various methodologies are employed to provide this capability while minimizing power consumption.

In general, there are three states relevant to a description of the present invention, though other operative states are not excluded. In the first, the telemetry module 14 of the IMD 10 is inactive. That is, the receiver 18 and transmitter 16 are powered down (or at the lowest possible operative capacity). The second state is referred to as session pending. The telemetry module 14 has been activated in some manner and some amount of data may have been transmitted and/or received, but a full telemetry session is not yet open. The third state is therefore an open telemetry session wherein the IMD 10 maintains open, active communication with a device such as programmer 40. In some embodiments, some data will be transmitted during every opportunity to transmit. In an alternative, low-energy mode, the synchronous communication session is maintained but any given window may pass without transmitting data.

Figure 3:
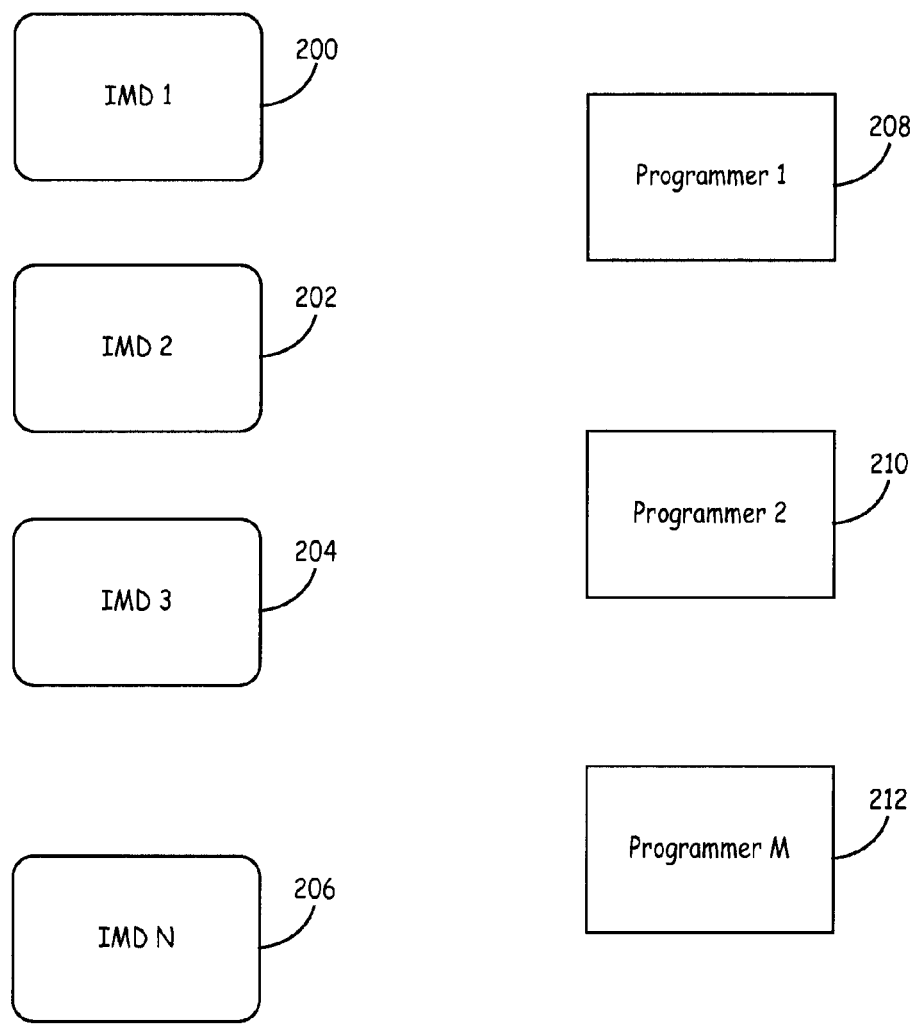
FIG. 3 is a schematic diagram illustrating a plurality of IMDs in a common environment with multiple programmers.

One advantage of distance telemetry is the ability to interrogate a plurality of patients in a common environment, such as a waiting room. FIG. 3 schematically illustrates N patients, each having an IMD 200-206, who are in, e.g., a clinic. The clinic has M programmers 208-212 that are available to interrogate patients. While the ability to interrogate the patients in this manner is advantageous, it does create some communication challenges.

In one embodiment, each patient has their device activated (e.g., 114 of FIG. 2) as they enter the waiting room. This causes each IMD 10 to activate a receiver so as to respond to an identification request from a given programmer 40. In order to mitigate the effects of noise or other interference, as well as to provide the ability for multiple devices to communicate simultaneously, the IMD 10 and programmer 40 each have multiple channels of communication to select from; that is, specific frequency ranges are assigned to a given channel and multiple channels are provided. As described herein, 10 channels are provided, though this is non-limiting.

The programmer 40 identifies a channel having the least noise or interference and selects that channel. The programmer 40 then transmits a signal on the selected channel that includes a programmer identification and a request that any IMD in the area identify itself. The programmer 40 listens for a response and, after a period of time (e.g., 5 seconds), will perform this process again. That is, determine the optimal channel and transmit the request for identification on that channel. The determined channel may or may not be the same as previously selected. Each IMD 10 is scanning through the ten channels. That is, the IMD 10 listens for a predetermined period of time on a given channel; if no message is received, it moves to the next channel.

If the request to identify is in fact received, then the IMD 10 will transmit (on that channel) a unique device identification. The programmer 40 responds to that IMD 10 transmission and requests patient-specific information stored within the IMD 10. The IMD 10 transmits that patient information, and then goes into a "silent" mode with respect to that programmer. In other words, the programmer 40 and IMD 10 have identified that the other is present, exchanged identification data, and established that communication is possible. While in the silent mode, the IMD 10 awaits subsequent instruction from the identified programmer 40. Other programmers 40 may send similar requests, and the IMD 10 may respond to multiple programmers. However, once this level of communication is achieved, that IMD 10 will not respond to subsequent general requests for identification from a programmer 40 that it has already identified itself to. Thus, with the example illustrated in FIG. 3, each programmer 208, 210, 212 may generate such requests and identify the presence of each of the IMDs 200, 202, 204, 206.

With multiple IMDs 10 present in a given environment, it is possible that more than one will be listening to a given channel at the same time, and as such, will be able to respond to the programmer's request for identification at the same time. To avoid data collision, each IMD 10 imposes a random delay prior to responding to the request for identification. As such, one IMD 10 will be able to respond sooner. During a subsequent transmission by the programmer 40 for a request for identification, the other IMD 10 will be able to respond. After each complete set of transmissions over all of the channels (e.g., 1-10), the programmer 40 imposes a random delay before beginning again.

As the programmer 40 transmits the request for identification on a given channel for a relatively long period of time, as compared to the amount of time a given IMD 10 listens to a channel, there is likely to be overlap within a relatively low number of attempts. That is, the IMD 10 scans the available channels and will be listening to the correct channel during a transmission from the programmer 40.

Figure 4:
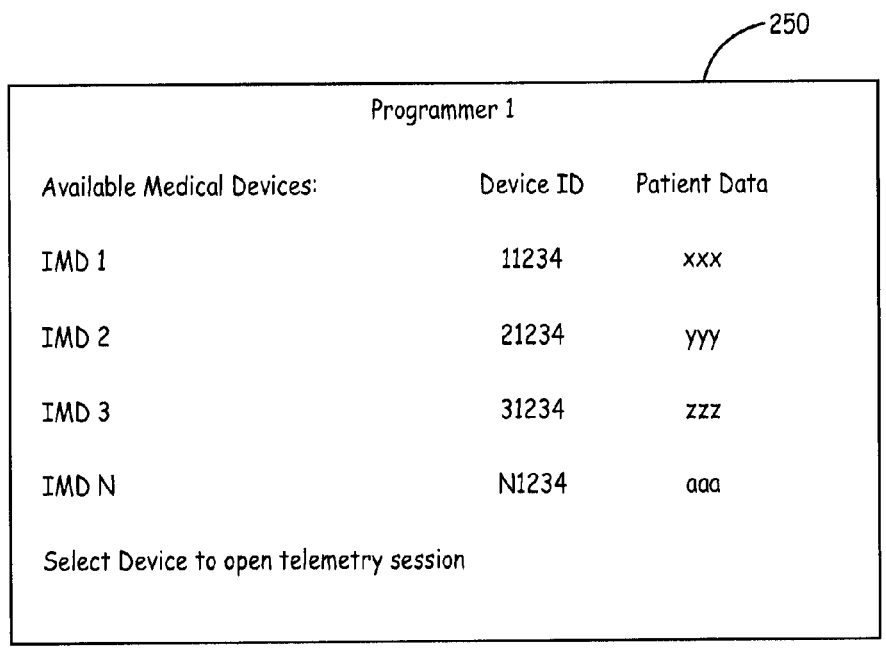
FIG. 4 is a representation of a sample screen from a programmer.

FIG. 4 represents a sample screen 250 from a given programmer 208 that has identified each of the IMDs 200, 202, 204, 206. As indicated, when the IMD 10 responded, it provided a unique identifier and patient data, which is displayed. Now, a specific device, e.g., IMD 1 is selected and an open session command is sent to IMD 1. The IMD 10 continues to scan the available channels and the programmer will determine the optimal channel; thus, the open session command is directed to a specifically identified IMD from a specific programmer 40 known to that IMD, but not necessarily on the same channel previously utilized. Proper receipt of this command synchronizes the timing of the programmer and the IMD 1. Once this session is established, there is a synchronized pattern followed wherein a specific period of time is allocated for programmer transmission (IMD receives) and IMD transmission (programmer receives). For any given window, there may or may not be data transmitted; however, each device is synchronized and is able to send and receive accordingly, as long as the session is open.

Figure 5:
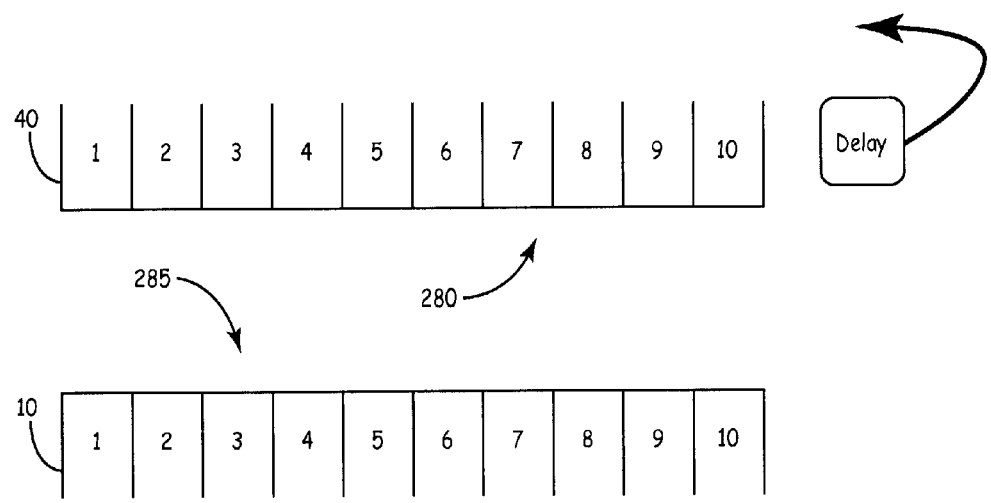
FIG. 5 is a schematic representation of channels available to two communicating devices.

FIGS. 5-8 illustrate certain of these concepts in greater detail. FIG. 5 illustrates the 10 channels 280 of programmer 40 and corresponding 10 channels 285 of IMD 10. As discussed, the programmer 40 will transmit a request for device identification and/or a request to open a session on a given channel identified as the best available at the time. After a predetermined period, the programmer 40 may reevaluate the available channels, select a channel and repeat the requests. It should be appreciated that, after the IMD 10 has identified itself to a particular programmer 40, the IMD 10 continues to check for other IMDs in the area. Thus, even though some form of communication has occurred on a specific channel, the IMD 10 is not then locked onto that channel. As such, subsequent asynchronous communication from the programmer 40 may occur at a time when the IMD 10 is scanning another channel. Alternatively, in some embodiments, the IMD 10 will only scan that specific channel at predetermined intervals; however, as there is no defined time as to when a subsequent transmission will occur, the receiver is powered off between these intervals to conserve power.

Figure 6:
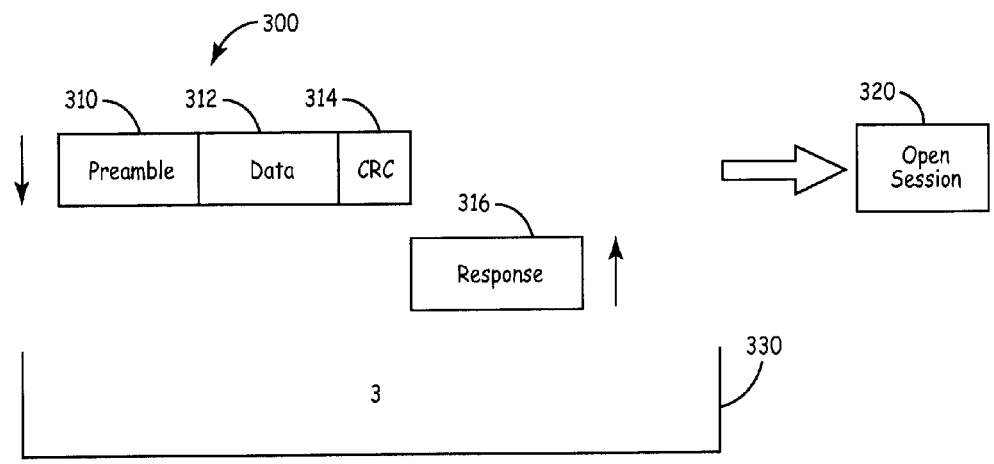

FIG. 6 illustrates how a request is successfully received and responded to by the IMD 10. Specifically, the request to open a session 300 is transmitted as a data packet having a preamble 310, data 312, and CRC 314 (cyclic redundancy code). The illustrated channel 3 window (of IMD 10) is the time allocated for both receipt of the request 300 from the programmer 40, and the subsequent transmission from the IMD 10. The termination point 330 of the window for channel 3 is indicated. In this example, the entire request 300 is received within the window. Responding to this message, the IMD 10 transmits the requested acknowledgement data packet in the form of response 316. As the response 316 is completely transmitted prior to termination 330 of the window for channel 3, the session is opened 320 on channel 3.

FIG. 7A illustrates the same message transmission 300 from the programmer 40 and response 316 from the IMD 10. FIG. 7B illustrates the termination 330 of the channel 3 window. In this example, the complete message 300 from the programmer 40 has been received; however, there was insufficient time for the IMD 10 to completely transmit the response 316. As such, the session is not opened on channel 3, and the device 10 continues to scan channels or powers down the receiver 18 for a predetermined interval. As one might appreciate, there are numerous possibilities as to how much information is received and/or transmitted prior to the termination 330. This may range from no part of message 300 occuring within the illustrated time window, to a single bit of the preamble 310 occuring, to the full message 300 and response 316 occurring as indicated in FIG. 6 with any incremental variation therebetween possible.

When the session in not opened, the IMD 10 will cycle through channels or cyclically check (a) specific channel(s) and the programmer 40 will continue to re-transmit the message 300 on the best available channel. As indicated, with a staggering of transmissions, the message 300, along with the time necessary to respond, will eventually fall within the window defined by the IMDs' scanning of channel 3, and the session will be opened.

This eventual overlap is assured due to the random delay on the transmission side and the consistent or non-randomized windows provided on the receiving side (or visa versa). If both were randomized, then there would exist the possibility that the request 300 would never be properly received by the IMD 10. On the other hand, multiple attempts may have to be made before a session is opened, causing the receiver 18 of the IMD 10 to use power. FIG. 7C illustrates an embodiment of the present invention, wherein the window in question is extended in some circumstances. In summary, the window, in this case for channel 3, will be extended when the IMD 10 is reasonably certain of a transmission from the programmer 40, thus mitigating the risk described above with respect to dual randomization.

In the embodiment of FIG. 7B, the entire response 316 from the IMD 10 must be provided prior to opening a session. In the embodiment of FIG. 7C, the window will be extended by providing an extension period 340 from initial termination point 330 to a modified termination point 332. The extension period 340 is added when the complete message 300 is received prior to the initial termination point 330. As the message 300 contains the preamble 310, data 312, and CRC 314, the IMD 10 is able to determine with a high degree of reliability that the message 300 is proper and that extending the window is appropriate. As such, the response 316 is provided at least in part during the extension period 340, and the session is opened 320.

Figure 8:
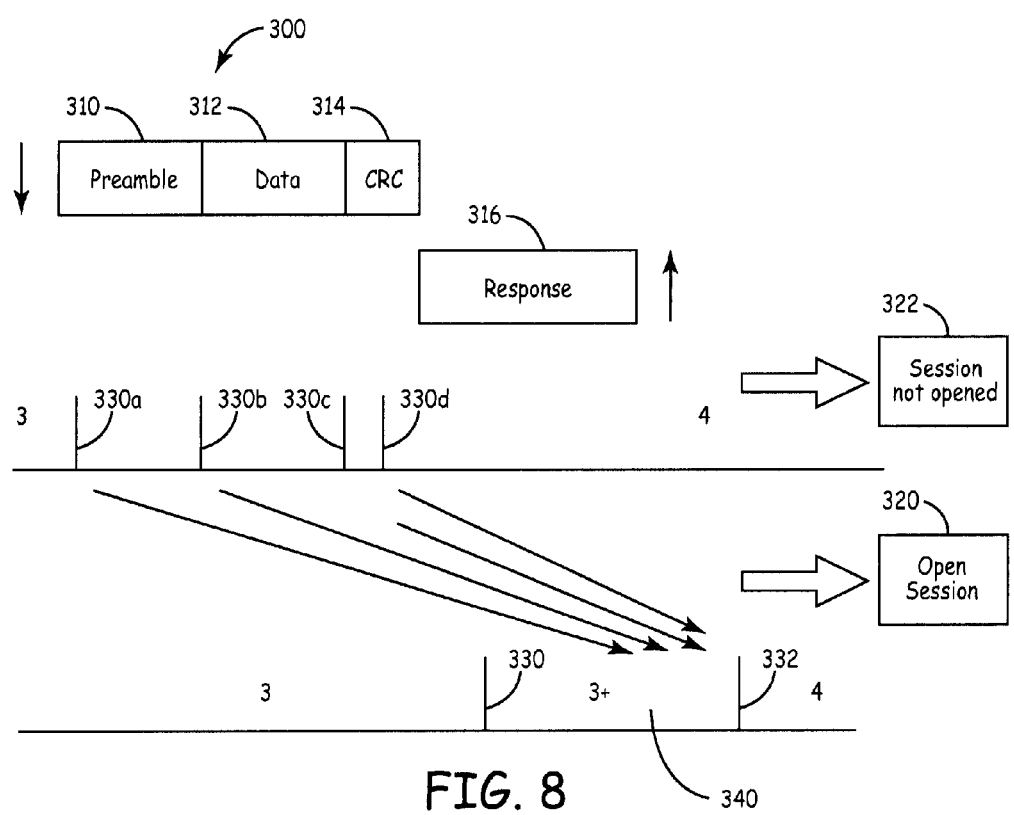

FIG. 8 illustrates alternative embodiments wherein less than the complete message 300 is received and the extension period 340 is added. If the initial termination point 330a occurs as illustrated, a single bit or only a few bits of the preamble 310 have been received. If the IMD 10 can determine with relative reliability that a partial transmission occurred, the receiver 18 will remain on and provide the extension 340 (not to scale) so as to provide enough time to complete reception and transmission of the response. This poses the most difficulty, in that making such a determination based upon a single bit or only a few bits of data may result in errors imposed by noise.

In another embodiment, the extension window 340 is utilized if the entire preamble 310 is received prior to termination point 330b. Since the preamble is a defined "word" and is verifiable by the IMD 10, the risk that noise is generating the message is significantly lowered. Thus, extending the window based upon a received preamble 310 is a relatively stable action. Termination point 330C illustrates that some or all of the data 312 is received prior to permitting the extension window 340 to be utilized. Similarly, termination point 330D indicates that at least all of the data 312 or some portion of the CRC 314 is received prior to extending the window. The degree of certainty required to confirm that the IMD 10 is in fact receiving message 300 will determine how much or how little of message 300 need be received before extending the active period for the receiver 18. The result is ultimately the opening 320 of a session between the IMD 10 and programmer 40 or EMD 50.

Figure 9:
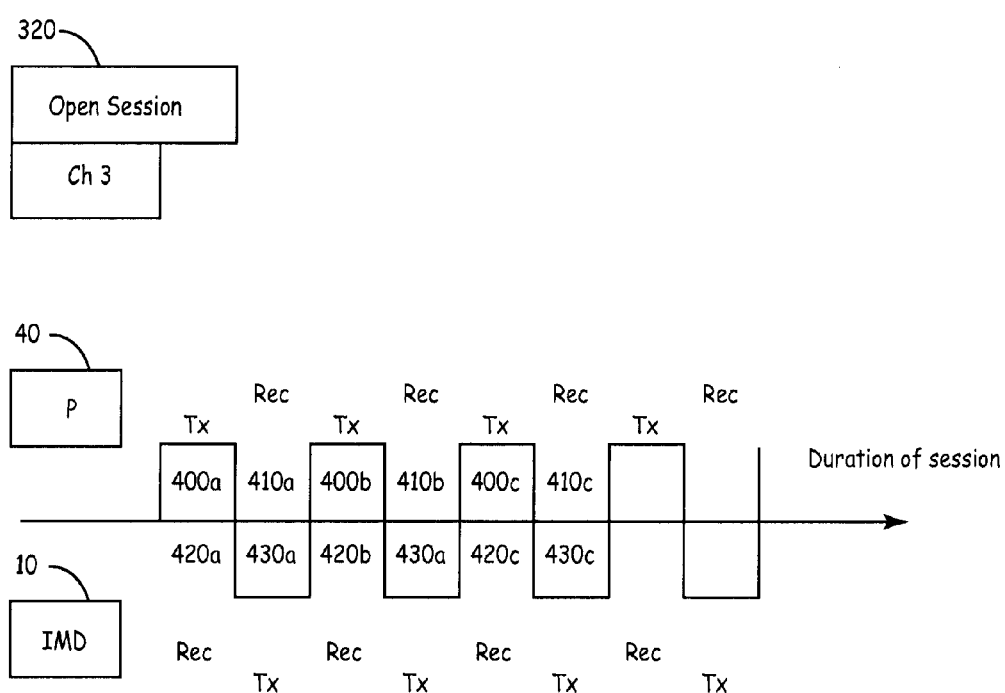
FIG. 9 is a schematic diagram illustrating synchronous communication.

During the process of opening the session 320, the communication moves from asynchronous to synchronous. This is accomplished by including various synch and clock data in a known manner. Thus, FIG. 9 schematically illustrates the synchronous nature of the open session 320. That is, predefined and correlated windows of time are established during which each of the IMD 10 and programmer 40 knows when they may transmit and when to receive. The transmission windows 400a, 400b, 400c, etc. of the programmer 40 correlate to the receive windows 420a, 420b, etc. of the IMD 10. Similarly, the receive windows 410a, 410b, of the programmer 40 correlate to the transmit windows 430a, 430b, etc. of the IMD 10.

These windows define when a given device may transmit data; however, they do not require that the device transmit data in every such window. As previously discussed, a session may be opened by a caregiver in a clinical setting, by a patient or caregiver for a remote interrogation, during the initial surgical implant of the IMD 10, by the IMD 10 for medical events, or for various other reasons. The duration of the open session will typically be long in comparison to the amount of time required for actual data transmission. Thus, many of the transmission windows could be fully or partially devoid of data.

In another embodiment, some data is transmitted during each available window. As will be discussed, the programmer 40 will always transmit a preamble that will convey information to the IMD depending upon whether the preamble is positively or negatively-correlated. The IMD 10 may operate in a variety of transmission modes. In one such mode, the transmitter 16 is only powered when the IMD 10 needs to transmit data, and one or more transmit windows 430 may be entirely devoid of transmission. In a low energy mode, certain data (e.g., real-time EGM or Marker Channel data) is transmitted during every transmit window 430. As this data will not require the use of the full window 430, the transmitter is powered down for a portion of the transmit window after this data is sent. Thus, at least some data will be transmitted by the IMD 10 in each such window 420. In a nominal mode, whatever data needs to be transmitted is so packaged and transmitted in the allotted time. In a maximum transmission mode, the programmer 40 indicates a desire to receive a particular block of data. In response, the IMD 10 transmits data over a period of time longer than a given window 430. As this has essentially been prearranged, the session remains synchronous and the programmer 40 knows that certain transmit windows 400 are being changed to receive windows 410. The duration of this elongated window need not be limited by technological considerations; however, it should not be so long that an emergency action initiated at the programmer 40 is delayed beyond a predetermined safety margin. In one example, the extended IMD transmit window 430 is approximately 119 milliseconds.

Figure 10:
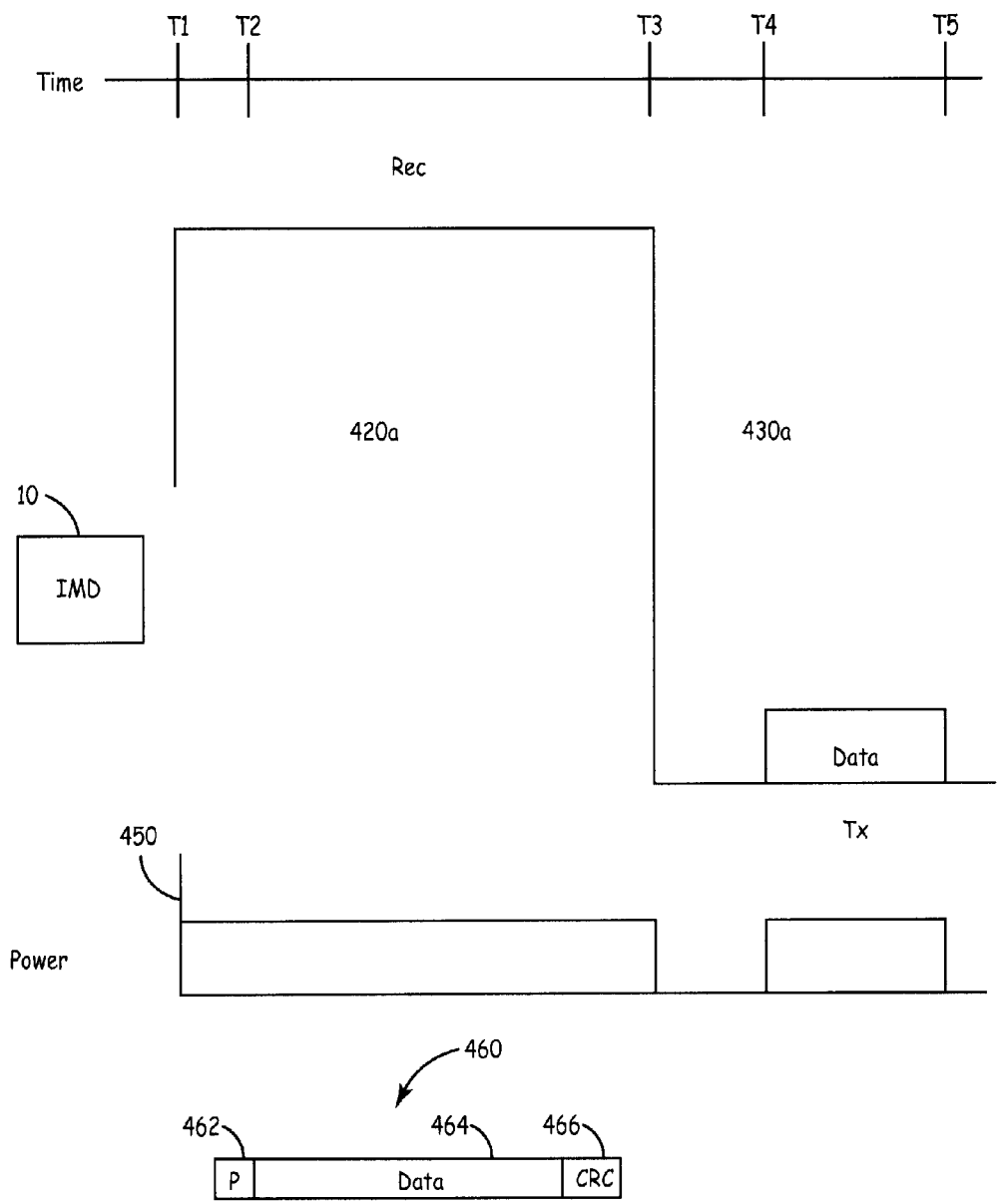
FIG. 10 is a schematic diagram illustrating one receive window and one transmission window.

The lack of data transfer during any given window is non-problematic and a synchronous open session is maintained. The programmer 40 does not have any particular power constraints. The IMD 10 only transmits when and what is deemed necessary, thus power is not utilized in transmit windows 430 where the IMD is not transmitting data. On the other hand, the receiver 18 is powered on for each of the receive windows 420, regardless of whether data is or is not transmitted by the programmer 40. These concepts are illustrated in FIG. 10, showing receive window 420a and transmit window 430a. As the IMD 10 does not know if a message 460 will be transmitted during window 420a, graph 450 indicates that power is provided to the receiver 18 during the entire window 420a, or from time T1 to time T3. At time T2, message 460 begins with a preamble 462, the data 464, and CRC 466 and is shown to terminate with the window at time T3. Thus, power is consumed by the receiver from T1 to T2, though no data is transmitted. During the transmit window 430a, the IMD 10 transmits data from time T4 to T5, and power for the transmitter is only necessitated for that interval.

FIG. 11a illustrates a graph 480 starting with time T1 corresponding to the initiation of receive window 420a. During this interval, no data is transmitted by the programmer 40 over the entire interval. In FIG. 11B, message 460 is transmitted during this interval. As indicated in FIG. 11C, the receiver 18 is on during the entirety of the window 420a in both examples. As such, power is provided to the receiver 18 whether or not data is being transmitted by the programmer 40.

FIGS. 11D and 11E illustrate an embodiment wherein power is conserved. In this embodiment, the programmer 40 will transmit preamble data during every transmit window 400, regardless of whether additional data is sent. The preamble is either a positively-correlated preamble 500 or a negatively-correlated preamble 520. Since the preamble is a specific encoding of data, the IMD 10 will recognize both the positive and negative correlation of the encoded data. A positive preamble 500 indicates to the IMD 10 that additional data will be forthcoming and the receiver 18 remains on 510 during the remainder of the window 420a. A negative preamble 520 indicates that the programmer 40 will not be transmitting additional data, thus the receiver 18 is powered down at time T2 and remains off for the duration of the window 540. In this manner, power consumption is reduced for each receive window 420 where a negative preamble is provided. The signal received is passed through the appropriate logic to determine whether the signal or its negative/inverse corresponds to the predefined preamble. If not, the signal is not the preamble. If so, then the signal is the preamble and whether it is the positive or negative correlation indicates whether to maintain power to the receiver 18.

This embodiment allows for the use of the predetermined preamble and only requires additional logic to identify a negative correlation of the same preamble. It should be appreciated that an alternative command 550 could be provided that is distinct from the preamble. As illustrated in FIG 11F, the receiver 18 is on 530 until time T2 when the alternative command 550 has been received. Subsequently, the receiver 18 is powered down 540 for the remainder of the interval. This embodiment requires the IMD 10 to recognize the preamble as well as the alternative command 550. The alternative command 550, if shorter in duration than the preamble, could result in additional power conservation.

Figure 12:
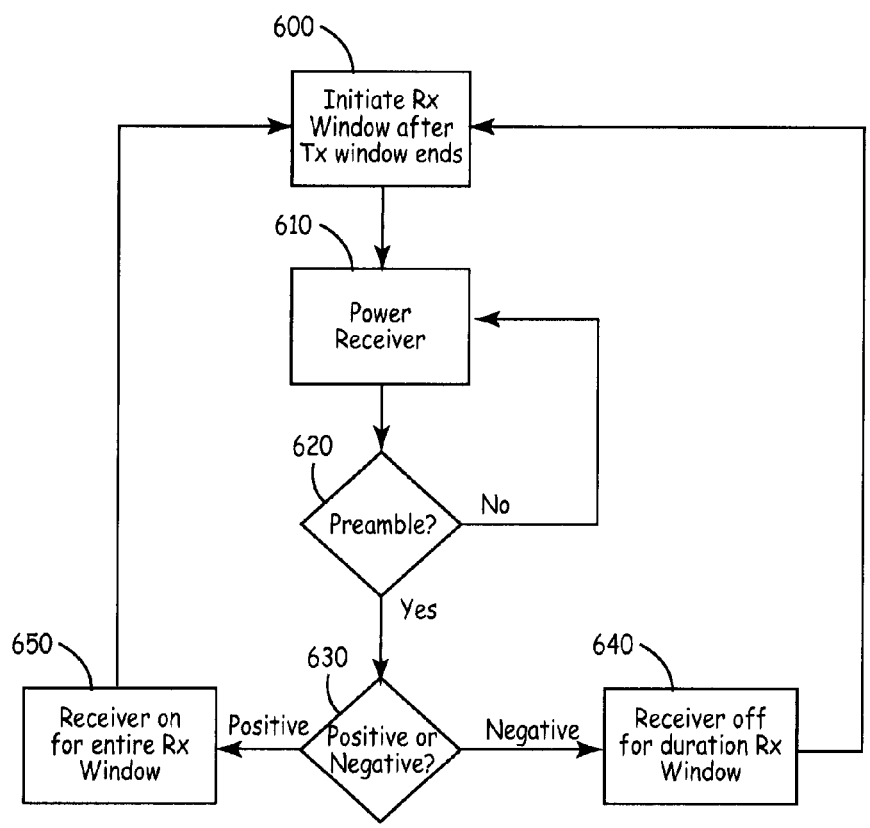
FIG. 12 is a flowchart describing a process for determining whether to maintain a receiver in a powered state.

FIG. 12 is a flowchart describing the above embodiments. A given receive window 420 begins (600) at the appropriate time. Accordingly, the IMD 10 powers (610) the receiver 18, which is then able to receive data. A determination is made as to whether data is received and, if so. whether that data is or is not the preamble (620). If not, then the receiver 18 remains on and continues to monitor. If the preamble was received (620), the IMD 10 determines (630) whether the preamble was a positive or negative correlation of the preamble. If negative, the IMD 10 powers down (640) the receiver 18 for the remainder of the window 420 and at the appropriate subsequent time, opens the next receive window (600) and the process is repeated. Alternatively, the preamble is positively-correlated (630); then the IMD 10 continues to power (650) the receiver 18 for the remainder of the window 420 to receive additional data. The process then returns to step 600. Though not illustrated, the transmission of the preamble by the programmer 40 is an indication of whether the programmer 40 will transmit additional data during the specific window. Thus, following a positively-correlated preamble, additional data should be sent and received by the IMD 10. Whether or not this occurs, the receiver 18 will be on and able to receive.

FIGS. 13 and 14 illustrate another embodiment of the present invention. FIG. 13 schematically illustrates the various transmit and receive windows previously discussed. In receive window 420*a*, the solid block indicates substantive data was received (or at least a positive preamble). In windows 420*b*-420*d*, a negative preamble was received, and thus the receiver 18 was powered down for a portion of each of those windows. Some number of consecutive cycles have elapsed, each with a negative preamble, as is the case with window 420E. As the programmer 40 has not indicated that it would send data for a given period of time, represented by the N consecutive cycles, the IMD 10 enters a more aggressive power-saving mode. In this mode, the receiver 18 will not be powered at all during a predetermined number of receive windows 420, beginning at time T1. At time T2, receive window 420 occurs and the receiver is powered in the normal manner. It should be appreciated that the condition for entering this mode, as well as the duration of the mode, may be based upon a number of cycles or specific periods of time.

FIG. 14 is a flowchart illustrating the aggressive power conservation mode. Steps 600-650 are similar to those of FIG. 12. When the receiver is powered down (640) for a portion of a cycle, an index value or counter is incremented (660). The value of the index is compared (670) to some predetermined value N. N may be any value and in one embodiment is 100 cycles (with a cycle meaning a receive window 420). In another embodiment, N is a time (e.g., 10 seconds) and the index is either converted to a time value or time is directly measured as the index. In any event, the index is compared to a predetermined value N (670). If the index is less than N, then the process returns to step 600 and is repeated. If the index equal or exceeds N, then the IMD 10 enters the aggressive power-conservation mode. This includes leaving the receiver 18 unpowered (680) for a specific number of cycles (or a specific duration). During this interval, any transmission from the programmer will go unreceived. Thus, the duration should not be so long that critical transmission will go unreceived for a period of time that leads to complications. Furthermore, the aggressive power conservation mode may be precluded by the caregiver through the programmer; that is, the feature may be disabled for the entire session or during parts of the session. This may be a preset function defined by a caregiver preference. Furthermore, the IMD 10 or programmer 40 may disable the aggressive conservation mode during any critical time periods, programming stages, when the IMD settings are vulnerable or in question, when particular therapies or activities are underway (e.g., threshold testing, inducing arrhythmias, defibrillation, etc.), or when the IMD 10 senses data of any nature that would require full communication (e.g., patient arrhythmia).

When the aggressive power-conservation mode is engaged, the receiver 18 is left powered down. The timing of the cycles is maintained so that a synchronous session remains open. Thus, when the receiver 18 is powered up at a later time, this occurs during a properly synchronized receive window 420.

Returning to the flowchart, the index value is modified (690) when the aggressive power-conservation mode is entered and the process returns to step 600 after the number of powered-down cycles or specific time elapses. The index value may be reset to 0, thus requiring the same N cycles (or time) to elapse before again re-entering the aggressive power-conservation mode. Alternatively, N may be reduced to some other value. Leaving N unchanged would result in only one receive cycle 420 occurring before re-entering the aggressive power-conservation mode. If the programmer was trying to transmit data, there are numerous reasons why that data may go unreceived for one cycle, and this may leave the programmer 40 unable to communicate with the IMD 10 for too long of a period. Thus, enough cycles 420 should be permitted to elapse to reliably determine whether the programmer 40 is attempting to transmit or not. The fact that the index has reached N once indicates a duration of inactivity, thus the index need not be reduced to 0 if the above allowance is made. In one embodiment, the index is modified (690) to N/2. Thus, half the time required to initially reach the aggressive power conservation mode is required to re-enter the mode subsequently.

Some minimum number of cycles (or duration) will be provided to assure that the IMD 10 powers the receiver 18 on for a sufficiently long period of time to reliably determine whether programmer transmission is or is not idle. While this value may depend on caregiver preferences or device specific parameters, assume for the present embodiment that this minimum is N/8. Thus, for each consecutive re-entry into the aggressive power conservation mode, the index may be modified (690) in a different manner. For example, the first such modification may be N/2, the second N/3, the third N/4, etc. This permits faster re-entry into the aggressive power-conservation mode with each successive iteration while always providing the minimum safe duration (e.g., N/8). Alternatively, N may be renegotiated between the programmer 40 (automatically or via the caregiver) and the IMD 10 based upon patient status, data transmission, or any number of parameters.

Returning to step 630, if a positively-correlated preamble is received, the IMD 10 powers (650) the receiver 18 for the duration of the interval 420. Now, there has been an indication that the programmer 40 is transmitting data and the index is set (700) to 0 and the process returns to step 600.

We claim:

1. An implantable medical device (IMD) having a telemetry module with a transmitter and receiver operable on a plurality of separate channels, the IMD comprising:
    means for selecting a given channel from the plurality of separate channels for a first predetermined period of time;
    means for operating the receiver on the given channel for the first predetermined period of time prior to establishment of a communication session with another medical device;
    means for analyzing data received on the given channel;
    means for determining if the data is indicative of a predetermined message; and
    means for extending the first predetermined period if the means for determining determine that the data is indicative of the predetermined message.

2. The IMD of claim 1, wherein the first predetermined period of time is allocated for reception of the predetermined message and transmission of a predetermined response by the IMD.

3. The IMD of claim 2, wherein the predetermined message includes a preamble, a data segment, and a cyclic redundancy code (CRC), and the predetermined response includes patient specific data.

4. The IMD of claim 3, wherein reception of the preamble, the data segment and the CRC are indicative of the predetermined message and the means for extending extend the predetermined time period to allow the IMD to transmit the predetermined response.

5. The IMD of claim 3, wherein reception of the preamble and the data segment are indicative of the predetermined message and the means for extending extend the predetermined time period to allow the IMD to transmit the predetermined response.

6. The IMD of claim 3, wherein reception of the preamble is indicative of the predetermined message and the means for extending extend the predetermined time period to allow the IMD to transmit the predetermined response.

7. The IMD of claim 1, further comprising means for scanning each of the plurality of separate channels sequentially and each for a duration equal to the first predetermined period of time.

8. The IMD of claim 7, further comprising means for opening a synchronous communication session if the predetermined message is received.

9. The IMD of claim 1, further comprising means for changing the receiver from an inactive state to an active state prior to operating the receiver on the given channel for the first predetermined period of time.

10. The IMD of claim 9, where the means for changing include means for sensing the status of an inductive coil.

11. A method of operating an implantable medical device (IMD) having a telemetry module, the method comprising:
selecting one of a plurality of available communication channels;
powering a receiver for a first predetermined period of time on the selected channel prior to establishment of a communication session with another medical device;
processing data received by the receiver on the selected channel during the first predetermined period of time;
transmitting a response message within the first predetermined time period if the processed data includes a predetermined message; and
extending the first predetermined period of time that the receiver remains on the selected channel if the processed data is indicative of the predetermined message.

12. The method of claim 11, further comprising switching the receiver to a second of the plurality of available channels at an expiration of the first predetermined period of time unless the first predetermined period of time is extended.

13. The method of claim 12, further wherein the first predetermined time period is only extended if the predetermined message is received in its entirety.

14. The method of claim 12, wherein the first predetermined time period is extended if a portion of the predetermined message is received.

15. The method of claim 14, wherein the portion is a preamble.

16. The method of claim 14, wherein the portion is a preamble and a portion of a data segment.

17. The method of claim 11, further comprising opening a synchronous communication session with transmission of the response method.

18. The method of claim 11, further comprising:
changing the receiver from an inactive state to an active state prior to powering the receiver on the selected channel.

19. The method of claim 18, further comprising sensing a state of an inductive coil, wherein a signal received on the inductive coil causes the IMD to change the receiver from the inactive state to the active state.

* * * * *